United States Patent
Thistle et al.

(10) Patent No.: US 8,353,947 B2
(45) Date of Patent: Jan. 15, 2013

(54) EVERSIBLE LOCKING MECHANISM FOR MODULAR STENTS

(75) Inventors: Robert C. Thistle, Bridgewater, MA (US); James B. White, Medfield, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 779 days.

(21) Appl. No.: 11/446,687

(22) Filed: Jun. 5, 2006

(65) Prior Publication Data

US 2006/0229704 A1 Oct. 12, 2006

Related U.S. Application Data

(62) Division of application No. 10/435,190, filed on May 9, 2003, now abandoned.

(51) Int. Cl.
*A61F 2/06* (2006.01)

(52) U.S. Cl. ...................................................... 623/1.13

(58) Field of Classification Search ................. 623/1.13, 623/1.16
See application file for complete search history.

(56) References Cited

U.S. PATENT DOCUMENTS

| | | | |
|---|---|---|---|
| 4,655,771 A | 4/1987 | Wallsten | |
| 5,522,881 A | 6/1996 | Lentz | |
| 5,609,627 A | 3/1997 | Goicoechea et al. | |
| 5,683,449 A | 11/1997 | Marcade | |
| 5,709,713 A | 1/1998 | Evans et al. | |
| 5,755,772 A * | 5/1998 | Evans et al. | 128/898 |
| 5,904,713 A * | 5/1999 | Leschinsky | 623/1.35 |
| 6,344,054 B1 | 2/2002 | Parodi | |
| 6,352,561 B1 | 3/2002 | Leopold et al. | |
| 6,383,214 B1 | 5/2002 | Banas et al. | |
| 6,524,335 B1 | 2/2003 | Hartley et al. | |
| 6,610,087 B1 * | 8/2003 | Zarbatany et al. | 623/1.32 |
| 6,719,781 B1 * | 4/2004 | Kim | 623/1.13 |
| 6,964,679 B1 * | 11/2005 | Marcade et al. | 623/1.13 |
| 2003/0088256 A1 * | 5/2003 | Conston et al. | 606/155 |
| 2003/0135258 A1 * | 7/2003 | Andreas et al. | 623/1.11 |
| 2003/0229389 A1 * | 12/2003 | Escano | 623/1.13 |
| 2003/0236567 A1 * | 12/2003 | Elliot | 623/1.13 |
| 2005/0010277 A1 * | 1/2005 | Chuter | 623/1.13 |

OTHER PUBLICATIONS

International Search Report of Application No. PCT/US2004/013509 dated Sep. 10, 2004.
Canadian Office Action in related Canadian Patent Application No. 2524855 dated Aug. 20, 2010. 8 pgs.

* cited by examiner

*Primary Examiner* — William H. Matthews
(74) *Attorney, Agent, or Firm* — Brooks, Cameron & Huebsch, PLLC

(57) ABSTRACT

The present invention provides an apparatus and method for locking self-expanding modular stent components together using an eversible extension on the male component. The male component is deployed partially within the female component, and with the eversible extension eversed over the male component.

19 Claims, 2 Drawing Sheets

EVERSIBLE LOCKING MECHANISM FOR MODULAR STENTS

CROSS-REFERENCE TO RELATED APPLICATION

This application is a Divisional Application of U.S. application Ser. No. 10/435,190 filed on May 9, 2003 and now abandoned.

TECHNICAL FIELD

This invention relates generally to luminal stents, and more particularly to a method and apparatus for providing a secure connection between components of a modular stent.

BACKGROUND OF THE INVENTION

Modular stents are used to treat luminal defects in a human body. For example, a modular stent comprising an aortic bifurcate component and an iliac limb component may be used to bypass an abdominal aortic aneurysm (AAA). In this exemplary modular stent, the aortic bifurcate component is a bifurcated female covered stent or stent-graft (sometimes referred to as a long leg-short leg) configured for placement in the aorta proximate the aortic bifurcation with a long leg extending into one of the iliac arteries and a short leg or stump extending into the other iliac artery. The iliac limb component is a male covered stent configured for placement in the iliac artery in which the short leg extends with its proximal end deployed within the short leg or stump. The stent in such combinations typically comprises an open framework or mesh of structural elements such as wires or thin metallic members, which may cross or intersect one another in various ways. In one such stent graft configuration, a braided stent is provided where opposing helical stent members overlap one another to form crossing intersections. Exemplary braided stents 10 are disclosed, for example, in U.S. Pat. No. 4,655,771 to Hans I. Wallsten, incorporated herein by reference. The braided stent is designed to be contracted radially for endoluminal placement into a patient and to self-expand radially into a configuration in which it urges the graft or covering against the wall of the body lumen in which it is disposed providing an open lumen. Using shape memory material for the braided stent members may provide this self-expansion. The graft in a stent-graft may be a covering or liner, disposed inside or outside of the stent and covering the stent to define a fluid passageway through the lumen of the stent.

It is important for the components of a modular stent to form a secure connection with each other to prevent relative movement of the components with respect to each other due to force exerted by blood flow, morphology of the lumen in which the modular stent is placed, or other factors. Also, with covered stents, if the connection is not sufficiently secure, these factors may cause leakage of bodily fluid between the modular components.

SUMMARY OF THE INVENTION

In accordance with an exemplary embodiment of the present invention, a modular stent system is connected by an eversible extension on the male component of the modular stent system. An eversible extension is formed on the male component by continued braiding of stent members used to form a self-expanding stent in the male component. The eversible extension is eversed or folded back over the self-expanding stent and radially restrained in the eversed position. The eversible extension and self-expanding stent are at least partially introduced into a lumen of a female component of the modular stent with the eversible extension radially constrained in an eversed position. The eversible extension and self-expanding stent are released or allowed to self-expand against the inner surface of the female component, locking the modular components together.

While the applicant will describe the invention in connection with preferred and alternative embodiments, it should be understand that the invention is not limited to those embodiments. Furthermore, one should understand that the drawings are not necessarily to scale. In certain instances, the applicant may have omitted details that are not necessary for an understanding of the present invention.

DETAILED DESCRIPTION OF THE INVENTION

The invention will next be described with reference to the figures wherein similar numbers indicate the same elements in all figures. Such figures are intended to be illustrative rather than limiting and are included herewith to facilitate the explanation of the apparatus of the present invention.

When used herein the following terms shall be understood to have the following meanings. The term proximal shall indicate a direction closer to a patient's heart, and the term distal shall indicate a direction farther from a patient's heart. The term stent shall indicate a generally tubular structural component for placement within a body lumen. The terms graft and covering shall indicate a flexible tubular member providing a passageway therethrough. The term stent-graft shall indicate a stent having a graft or covering attached thereto. Everse shall mean to roll or pivot a tubular member inside out.

Figure 1:
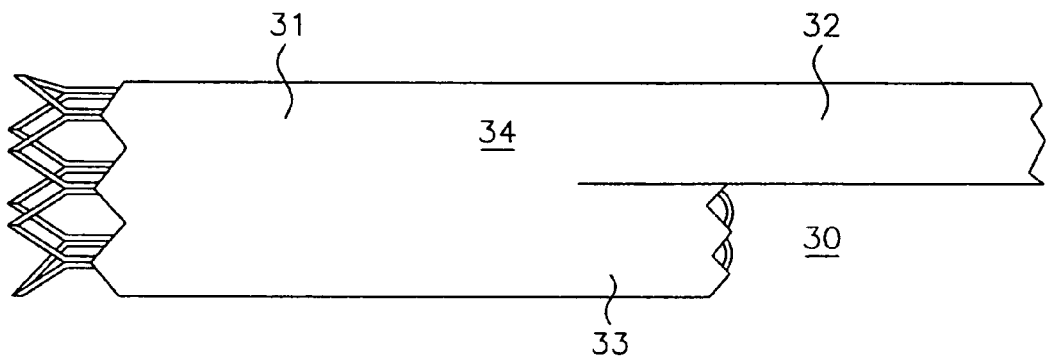
FIG. 1 is a bifurcate female component of a modular stent-graft.
Figure 2:
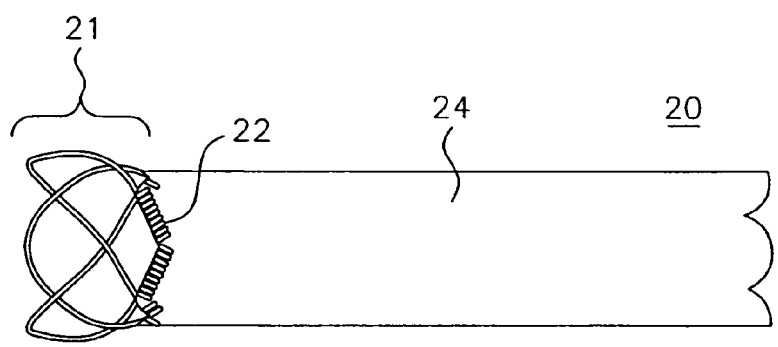
FIG. 2 is a male component of a modular stent-graft with an eversible extension according to an exemplary embodiment of the present invention.

FIGS. 1 and 2 show a female component 30 and a male component 20, respectively, of a modular stent-graft, according to an exemplary embodiment of the present invention. Male component 20 is configured to be deployed partially within female component 30 to form the modular stent-graft. Female component 30 is a bifurcated covered stent having a trunk 31 in fluid communication with a long leg 32 and a short leg 33. Trunk 31 is configured for placement in an abdominal aorta, long leg 32 is configured for placement in a first iliac artery, and a short leg or iliac stub 33 is configured to extend into a second iliac artery. Male component 20 is an iliac limb configured to be deployed with its proximal end within the iliac stub 33 of the female component to form a modular stent-graft. Both, male component 20 and female component 30, comprise a self-expanding stent (not shown), preferably a braided stent with a graft or covering 24,34 attached thereto. In an exemplary embodiment of the invention, covering 24 is lashed or stitched to the stent of male component 20 using a filament 22. While a modular stent-graft is illustrated and described, such as is used for treating an aneurysm, an uncovered modular stent system is contemplated within the scope of the present invention. An uncovered modular stent system, for example, might be used to treat stenosis. Also, while a braided self-expanding stent is described other self-expanding stent configurations are contemplated within the scope of the present invention.

Each self-expanding stent preferably comprises intersecting stent members, which are preferably helical braided to form a tubular stent. An exemplary braided stent comprises a first set of stent members wound in a first helical direction and a second set of stent members wound in a second, opposite helical direction, forming a plurality of intersections. The first and second sets of stent members may be continuous stent members with reversing axial direction at the ends of male and female components. These stent members may be wire, such as nitinol or stainless steel, or may comprise polymer or any other stent material known in the art. Shape memory material such as nitinol, however, is preferred.

Figure 3:
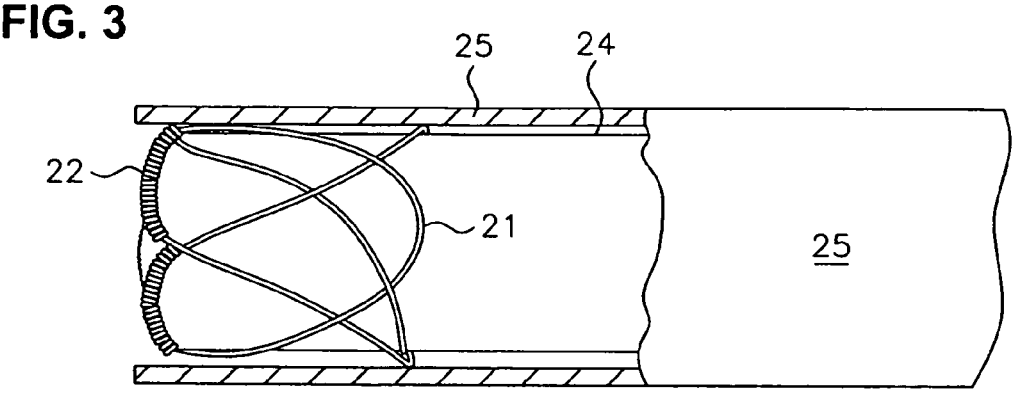
FIG. 3 is a cut-away view of a delivery sheath constraining the male component of FIG. 2 showing the eversible extension constrained in an eversed position by the delivery sheath.

An eversible stent extension 21 extends from the stent in the male component 20. Eversible stent extension 21 is preferably formed by continuation of the braided stent members forming the self-expanding stent of male component 20. Eversible stent extension 21 is configured to be eversed or pivoted back over the self-expanding stent, and held in this eversed position by a delivery sheath 25 (FIG. 3). Eversible stent extension 21 is next deployed within the female component 30, the delivery sheath 25 is withdrawn, and the eversible stent extension 21 in an eversed position locks the modular stent-graft components together. The modular stent components are connected by friction between the outer surface of the male component 20 and the inner surface of the female component 30. This friction is caused by outward force exerted by the self-expanding stent of the male component and inward force exerted due to the hoop strength of the female component and/or the wall of the body lumen.

Eversible stent extension 21 is pivoted outwardly and back over the male component 20, as shown in FIG. 3. Each stent member which continues into the eversible stent extension is bent at a circumferential series of locations around the stent of male component 20 to everse the eversible stent extension 21. To facilitate this eversion, eversible stent extension 21 may be outwardly flared from the diameter of the stent in male component 20 to create a greater torsional force on the stent members. Also, eversible extension 21 is preferably uncovered. In an exemplary embodiment of the present invention, eversible stent extension 21 is eversed by bending it back over the stent of male component 20. After eversible extension 21 is eversed, it is introduced into a delivery sheath 25 in an eversed configuration, as shown in FIG. 3, for endoluminal delivery into a body lumen.

As shown in FIG. 3, where male component 20 is a stent-graft, eversible extension 21 is preferably eversed at the end of covering 24. The end of covering 24 is preferably stitched or lashed to the stent members circumferentially around the stent, such as with a continuous filament 22. The continuous filament may be knotted around intersecting stent members. The filament may be a suture or a wire, or other material having sufficient flexibility for lashing and knotting and sufficient strength to attach a graft on a stent.

Figure 4:
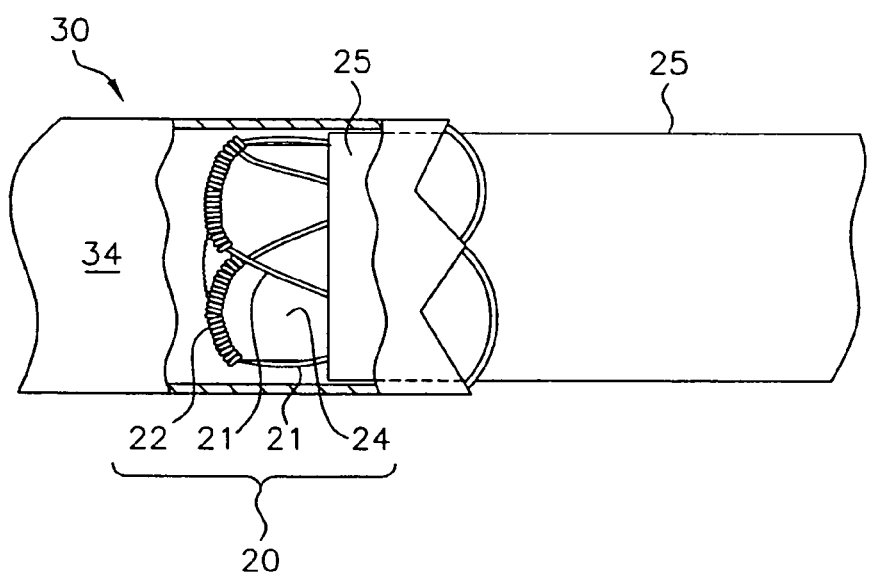
FIG. 4 is a partial cut-away view of the delivery sheath of FIG. 3 and male component of a modular stent-graft advanced into the female component of the modular stent-graft with the male component of the modular stent graft partially deployed within the female component.

Referring now to FIG. 4, delivery sheath 25 is extended into female component 30, with male component radially constrained within the delivery sheath 25 and eversible stent extension 21 restrained by delivery sheath 25 in an eversed configuration. When male component 20 is at the desired location (extending into female component 30), delivery sheath 25 is axially withdrawn along male component 20. As shown in FIG. 4, the exposed portion of male component 20 expands outwardly against the inner surface of female component 30. The location of male component 20 may be determined using, for example, radiography or the like. Delivery sheath 25 is withdrawn from male component 20 until the full length of male component 20 is free from delivery sheath 25, and male component is allowed to self-expand along its entire length, with eversible stent extension 21 still eversed over covering 24.

Figure 5:
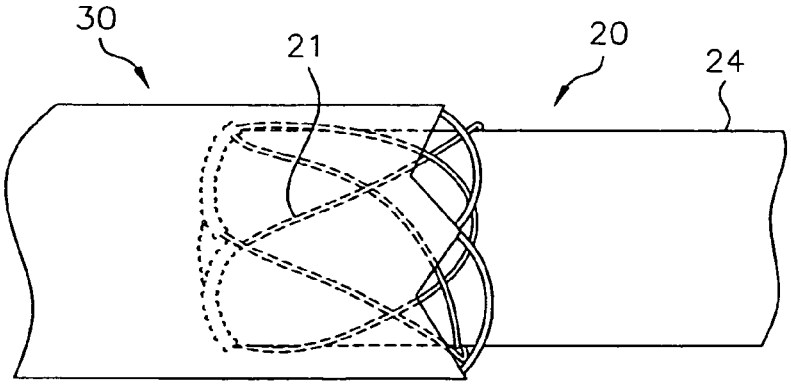
FIG. 5 shows a modular stent-graft in which the female component and male component are connected by the eversible extension of the male component according to an exemplary embodiment of the present invention.

FIG. 5 shows a connected modular stent-graft according to an exemplary embodiment of the present invention. The proximal end of male component 20 is placed within the iliac stub 33 of female component 30 with eversible extension 21 eversed. The outward forces exerted by the self-expanding stent and by the eversible extension trying to return to a non-eversed configuration lock the male component 20 inside the female component 30.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A modular stent-graft system comprising:
   a self-expanding bifurcated female stent-graft component having a lumen therethrough comprising a trunk, a leg, and a stump shorter than said leg configured for receiving a male stent-graft; and
   a self-expanding male stent-graft component having a proximal end partially positioned within and locked with said lumen of said female stent-graft component;
   said proximal end having an eversed stent extension at the proximal end of said male stent-graft component, wherein the eversed stent extension is formed from stent members that form the male stent-graft component and is in the eversed configuration upon the male stent-graft component prior to deployment within said female stent-graft component to lock said male stent-graft component to an inner surface of said female stent-graft component with an outward force exerted by the self-expanding stent and the eversed stent extension attempting to return to a non-eversed configuration,
   said male stent-graft component having a covering attached thereto, and
   said eversed stent extension being uncovered, wherein the eversed stent extension contacts the covering in the eversed configuration.

2. The modular stent-graft system of claim 1 wherein said male stent graft component comprises a self-expanding stent with a covering lashed thereon.

3. The modular stent-graft of claim 2 wherein said self-expanding stent comprises one or more braided filaments.

4. The modular stent-graft of claim 3 wherein said eversed extension comprises a continuous braiding of at least one of said one or more braided filaments.

5. The modular stent-graft system of claim 1 wherein, prior to eversing said eversed extension, said eversed extension is flared outwardly.

6. The modular stent-graft system of claim 1 wherein said female stent-graft is a bifurcated stent-graft comprising a trunk configured for placement in an abdominal aorta, an iliac leg configured for placement in a first iliac artery, and an iliac stump shorter than said iliac leg and configured for placement in a second iliac artery and for receiving said male stent-graft.

7. A method for implanting said male and female components of the modular stent-graft of claim 1 comprising the steps of:
- endoluminally delivering said female stent-graft component into a body lumen;
- providing said male stent-graft component with an eversible extension;
- eversing said eversible extension over said male stent-graft component;
- radially restraining said eversible extension in an eversed position;
- endoluminally positioning said male stent-graft component and said eversed extension partially within said female stent-graft component; and
- releasing said eversed extension to lock said male stent-graft component into said female stent-graft component.

8. The method of claim 7 wherein said eversed extension is restrained by an axially movable delivery sheath.

9. The method of claim 8 wherein said eversed extension is released by axially withdrawing said delivery sheath.

10. The method of claim 7 wherein said eversible extension is flared outwardly such that it is eversed by introducing said male stent-graft component into a delivery sheath.

11. A locking mechanism for use in a modular self-expanding stent comprising:
- a bifurcated female stent component comprising a trunk, a leg, and a stump shorter than said leg configured for receiving a male stent-graft;
- a male stent component deployed and locked partially within a lumen of said female stent component, said male stent component having a covering attached thereto; and
- an uncovered eversed stent extension extending from said male stent component formed from stent members that form the said male stent component, said eversed stent extension in an eversed configuration upon said male stent component prior to being deployed within said mating female stent component to lock said male stent component to an inner surface of said female stent component with an outward force exerted by the self-expanding stent and the eversed stent extension attempting to return to a non-eversed configuration, wherein the eversed extension contacts the covering in the eversed configuration.

12. The locking mechanism of claim 11 further comprising said covering attached to said male stent component, and a covering attached to said female stent component to form a modular stent-graft.

13. The locking mechanism of claim 12 wherein said modular stent system is configured for deployment in an abdominal aorta, spanning the aortic bifurcation.

14. The locking mechanism of claim 11 wherein said eversed stent extension is outwardly flared prior to placement within a delivery sheath in the eversed configuration.

15. The locking mechanism of claim 11 wherein said male stent component comprises one or more braided filaments.

16. The locking mechanism of claim 15 wherein said eversed extension is formed by continued braiding of one or more of said braided filaments of said male stent component.

17. The locking mechanism of claim 16 wherein a covering is lashed to said male stent component to form a stent-graft and said eversed extension extends beyond said covering.

18. The locking mechanism of claim 11 in combination with a delivery sheath, said sheath configured to temporarily hold said eversed stent extension in said eversed configuration until said male stent component is deployed partially within the lumen of said female stent component.

19. A modular stent-graft system comprising:
- a self-expanding bifurcated female stent-graft component having a lumen therethrough comprising a trunk, a leg, and a stump shorter than said leg configured for receiving a male stent-graft; and
- a self-expanding male stent-graft component having a covering attached thereto and having a proximal end positioned within and locked with said lumen of said female stent-graft component;
- said proximal end having an uncovered eversed stent extension formed from stent members that form the male stent-graft component, said extention being positioned within said female stent-graft component in an eversed configuration, said eversed stent extension being in the eversed configuration prior to being positioned within said female stent component, to lock said male stent-graft component to an inner surface of said female stent-graft component with an outward force exerted by the self-expanding stent and the eversed stent extension attempting to return to a non-eversed configuration, said eversed stent extension comprising a continuous braiding of at least one braided filament, wherein the eversed stent extension contacts the covering in the eversed configuration.

* * * * *